(12) United States Patent
Thorne et al.

(10) Patent No.: US 11,524,016 B2
(45) Date of Patent: Dec. 13, 2022

(54) COMPOSITIONS AND METHODS FOR THE TOPICAL ADMINISTRATION OF SPIRONOLACTONE FOR THE TREATMENT OF CUTANEOUS SIGNS OF EXCESS ANDROGEN AND CHRONIC STRESS RESPONSE

(71) Applicants: Amy Thorne, Ardmore, OK (US); Tien Viet Nguyen, Seattle, WA (US)

(72) Inventors: Amy Thorne, Ardmore, OK (US); Tien Viet Nguyen, Seattle, WA (US)

( * ) Notice: Subject to any disclaimer, the term of this patent is extended or adjusted under 35 U.S.C. 154(b) by 0 days.

(21) Appl. No.: 16/931,828

(22) Filed: Jul. 17, 2020

(65) Prior Publication Data

US 2022/0016134 A1 Jan. 20, 2022

(51) Int. Cl.
*A61K 31/585* (2006.01)
*A61P 17/14* (2006.01)
*A61P 17/08* (2006.01)

(52) U.S. Cl.
CPC ............ *A61K 31/585* (2013.01); *A61P 17/08* (2018.01); *A61P 17/14* (2018.01)

(58) Field of Classification Search
CPC ......... A61K 31/585; A61P 17/08; A61P 17/14
See application file for complete search history.

(56) References Cited

U.S. PATENT DOCUMENTS

| 5,506,222 A | 4/1996 | Stefano et al. |
| 2006/0067892 A1* | 3/2006 | Vergnault ............... A61K 9/146 424/46 |

FOREIGN PATENT DOCUMENTS

| EP | 0124147 | 11/1984 |
| EP | 410348 | * 7/1990 |
| EP | 0582458 | 11/1995 |

OTHER PUBLICATIONS

Motosco et al. (British journal of Dermatology (2019), 180, pp. 26-30) (Year: 2019).*
Ragmanauskaite et al., "Acne and the Lesbian, Gay, Bisexual, or Transgender Teenager," Dermatol Clin, 2019, 8 pages.

* cited by examiner

*Primary Examiner* — Savitha M Rao
(74) *Attorney, Agent, or Firm* — Polsinelli PC

(57) ABSTRACT

The present disclosure provides methods for treating or alleviating symptoms of a disease, disorder, or condition related to excess androgen or stress-induced skin changes in a subject in need thereof by topically administering a pharmaceutical composition comprising a pharmaceutically effective amount of spironolactone to the subject. Other aspects relate to methods for providing anti-oxidative stress, anti-inflammatory and anti-aging benefits for the skin to a subject in need thereof by topically administering a pharmaceutical composition comprising a pharmaceutically effective amount of spironolactone to the subject. Surprisingly, it has been found that spironolactone may be topically administered with reduced adverse effect compared to systemic administration of the same medication.

4 Claims, No Drawings

COMPOSITIONS AND METHODS FOR THE TOPICAL ADMINISTRATION OF SPIRONOLACTONE FOR THE TREATMENT OF CUTANEOUS SIGNS OF EXCESS ANDROGEN AND CHRONIC STRESS RESPONSE

FIELD OF THE INVENTION

The present invention relates to compositions comprising spironolactone and methods of using the same.

BACKGROUND OF THE INVENTION

Spironolactone is known for various medical applications and indications as an orally administered medication. For instance, high doses of oral spironolactone have been used in the treatment of acne vulgaris as well as hirsutism (Shaw, J. C., *J. Am. Acad. Dermat.* 24:236-243, 1991). Unfortunately, the systemic administration of spironolactone has resulted in a number of adverse effects, including irregular menstruation, arrest and/or reversal of the development of secondary sexual characteristics, total volume depletion due to diuresis, nausea, dizziness, etc.

More recently, topically administered spironolactone has been investigated for use in the treatment of acne vulgaris. However, results from these studies have been limited and conflicting in terms of outcome.

As such, there remains a need for improved compositions and methods for topically administering spironolactone.

SUMMARY OF THE INVENTION

The present disclosure provides compositions and methods for topically administering spironolactone to a subject in need thereof, wherein the compositions and methods result in reduced adverse effects, as compared to systemic administration.

In certain embodiments, the compositions and methods are for the treatment or alleviation of the signs and symptoms of diseases, disorders, or conditions related to excess androgen in both men and women. By way of example, the disease, disorder, or condition of interest may be selected from those patients receiving sex hormone replacement, including but not limited to patients with polycystic ovarian syndrome (PCOS), metabolic syndromes, congenital adrenal hyperplasia, patients undergoing gender reassignment, or those receiving sex hormone due to total orchiectomy after testicular cancer or gonadal failure. In other embodiments, the disease, disorder, or condition of interest may include those wherein excess androgen produces undesirable cutaneous outcomes in patients, including unwanted hair growth, acne eruptions, and premature senescence of the skin, which presents in a myriad of ways including but not limited to hyper and hypopigmentation, atrophy and laxity, and rhytids.

In other embodiments, the present disclosure provides methods for the treatment or alleviation of symptoms of a disease, disorder, or condition related to excess androgen, the method comprising topically administering a pharmaceutical composition comprising an effective amount of spironolactone to a subject in need thereof. In certain embodiments, the pharmaceutical composition comprises from about 5% to about 25% spironolactone by weight of the total composition.

DETAILED DESCRIPTION OF THE INVENTION

As discussed in further detail herein, the present disclosure provides compositions and methods for topically administering spironolactone to a subject in need thereof, wherein the compositions and methods result in reduced adverse effects. In certain aspects, the compositions and methods are useful in treating skin diseases in special patient populations with reduced adverse effects, for the purpose of achieving the desired clinical outcomes while maximizing subject safety.

Surprisingly, it has been found that spironolactone may be topically administered to provide for the treatment or alleviation of signs and symptoms of a disease, disorder, or condition related to excess androgen or stress-induced skin changes in a subject in need thereof, with reduced adverse effect compared to systemic administration.

The section headings are used herein for organizational purposes only and not to be construed as in any way limiting the subject matter described.

Definitions

As used herein, excess androgen refers to an endocrinologic state associated with levels of androgens beyond those deemed to be clinically normal or effective, typically producing unwanted outcomes. This can affect people of any age and gender, with a predilection for younger females. In certain aspects, the disclosure includes cutaneous signs of excess androgen production, which may manifest as inflammatory papules, pustules, comedones, nodules, cysts, excess hair or inappropriate hair production (hirsutism), premature hair loss (alopecia), redness (erythema), and excessive oil secretion with or without superimposed fungal/yeast infection (seborrhea). In accordance with the disclosure, diseases, disorders and conditions causing excess androgen include, but are not limited to: sex hormone replacement, PCOS, metabolic syndrome, congenital adrenal hyperplasia and other inborn errors of steroidogenesis and metabolism, pituitary, thyroid, or gonadal diseases, puberty syndromes, and iatrogenic Cushingoid syndromes seen in patients regularly receiving corticosteroids.

In the context of the present disclosure, "spironolactone" has the following chemical structure:

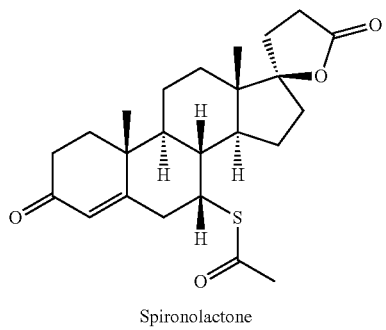

Spironolactone

As recognized by those of skill in the art, spironolactone may also be referred to as, SC-9420; NSC-150339; 7α-acetylthiospirolactone; and 7α-acetylthio-17α-hydroxy-3-oxopregn-4-ene-21-carboxylic acid γ-lactone.

As used herein, the term "pharmaceutically acceptable excipient" refers to an excipient for administration of a pharmaceutical agent, and includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences).

Methods of Topical Administration

The present disclosure provides methods for topically administering a pharmaceutical composition comprising a pharmaceutically effective amount of spironolactone to a subject in need thereof, wherein the methods result in reduced adverse effects compared to systemic administration. Surprisingly, it has been found that spironolactone may be topically administered to provide for the treatment or alleviation of symptoms of a disease, disorder, or condition related to excess androgen in a subject in need thereof, with reduced adverse effect compared to systemic administration of the same medication.

In certain embodiments, the methods are for the treatment or alleviation of symptoms of a disease, disorder, or condition related to excess androgen. By way of example, the disease, disorder, or condition related to excess androgen may be selected from patients receiving sex hormone replacement, PCOS, metabolic syndrome, congenital adrenal hyperplasia, or seborrheic dermatitis.

In other embodiments, the present disclosure provides methods for the treatment or alleviation of symptoms of a disease, disorder, or condition related to excess androgen, the method comprising topically administering a pharmaceutical composition comprising an effective amount of spironolactone to a subject in need thereof. In certain embodiments, the pharmaceutical composition comprises from about 5% to about 25% spironolactone by weight of the total composition, about 5.1% to about 25% spironolactone by weight of the total composition, about 7.5% to about 25% spironolactone by weight of the total composition, about 10% to about 25% spironolactone by weight of the total composition, etc.

Without intending to be limited by theory, in accordance with aspects of the disclosure, spironolactone may exert its biological effects in the treatment and alleviation of symptoms of diseases, disorders, or conditions related to excess androgen via action on the pilosebaceous unit, which includes the entire structure of the hair follicle and its associated glands.

In certain aspects, the effective topical administration of spironolactone may affect the microflora of the pilosebaceous unit. Without intending to be limited by theory, a reduction in the production of sebum from the sebocytes (those cells in the skin which have multiple hormone receptors) will potentially prevent the growth of pathogenic microflora, including yeasts, bacteria, and other microorganisms thought to feed on sebum, such as *Demodex* mites.

In particular, certain embodiments of the disclosure relate to the treatment of conditions involving the skin microflora of the genus *Malassezia*, such as seborrheic dermatitis and different forms of rosacea. *Malassezia* (former name *Pityrosporum*) is a normal yeast found on human skin, but in some individuals this microflora causes pathologic skin findings, including but not limited to acneiform eruptions, *pityrosporum* folliculitis, generalized pruritus in the elderly and children, exacerbated atopic dermatitis of the head and neck in adolescents and adults, and cradle cap in infants.

Seborrheic dermatitis is a ubiquitous, chronic, inflammatory skin condition affecting any age group and is associated with high psychological morbidity. Furthermore, seborrheic dermatitis disproportionately affects subjects under high psychological stress, as well as subjects with neurodegenerative diseases such as multiple sclerosis, Parkinson's disease, and subjects who have had spinal cord injuries or strokes, and subjects with HIV-AIDS regardless of treatment status.

In another aspect, topical spironolactone may provide anti-oxidative stress, anti-inflammatory and anti-aging benefits for the skin. Unlike previous anti-androgen drugs used to treat acne vulgaris, which did not possess any anti-mineralocorticoid or anti-glucocorticoid effects, in accordance with aspects of the disclosure, topical spironolactone exhibits anti-oxidative, anti-inflammatory and anti-aging effects. Without intending to be limited by theory, topical spironolactone is believed to achieve such anti-oxidative, anti-inflammatory and anti-aging benefits by virtue of its ability to act on not only the androgen receptors, but also the glucocorticoid and mineralocorticoid receptors.

Aldosterone is a mineralocorticoid hormone produced by the adrenal glands. It primarily acts on the sodium channels of the renal tubules to increase water and ion absorption, thus resulting in an increase in blood pressure that in turn provides an important mechanism for the cardiovascular system to respond to physiologic stress. As such, its activity has major effects on the vasculature, heart, and kidneys. Aldosterone has been implicated in oxidative stress, chronic inflammation, and scarring (fibrosis) of the heart, kidneys, and vascular system (Brown, N. J. *Curr Opin Nephrol Hypertens.* 14(3):235-41). By competing for the same biding site on the mineralocorticoid receptors in the renal tubules, spironolactone inhibits the actions and thus downstream effects of aldosterone on its targets.

In accordance with certain aspects of the disclosure, topical spironolactone exerts activity on the structures of the skin, which also suffer chronic damage from systemic stress and inflammation. Without intending to be limited by theory, the influence of hormones and pro-inflammatory chemokines is implicated, as sebaceous glands are miniature neuroendocrine organs embedded within the skin. As such, in certain aspects of the disclosure, topical use of spironolactone may effectively reduce oxidative stress and end-organ damage of the skin via its actions on the androgen, glucocorticoid, and mineralocorticoid receptors. In other words, topical use of spironolactone has anti-oxidative-stress and anti-aging benefits for the skin, while sparing its systemic effects on unintended organs, thus allowing for fewer to no adverse effects.

As mentioned above, spironolactone has affinity for the glucocorticoid receptor (anti-inflammatory), the androgen receptor (anti-androgen), and the mineralocorticoid receptor (anti-stress). Its real-world use could benefit several skin conditions in the general population as well as in subpopulations of patients undergoing high oxidative stress, including but not limited to those receiving systemic chemotherapies, humans exposed to increased amounts of UV radiation, air pollution, and even chronic psychological stress states, such as those experiencing post-traumatic stress disorder.

In its topical form, spironolactone may be used as a preventative agent to maintain youthful skin thickness, color, and texture. As such, in certain aspects the composition and methods provide an anti-aging topical agent comprising spironolactone, optionally to be used in concert with other well-known preventative topical products, such as sunscreens.

While it would certainly not address the known stressor for the patient, nor the psychiatric comorbidity, the use of topical spironolactone may prevent long lasting physical changes in the skin, which in turn can cause long-term psycho-social morbidity such as shame, body dysmorphia, and the ability to maintain gainful employment if the patient is stigmatized by skin disease. In certain aspects, the compositions and methods of the disclosure may be used in concert with other psychiatric and psychological modalities, as well as to prevent skin changes and possibly the comorbid psychiatric conditions as patients undergo extreme physical stressors such as cancer treatments.

In other embodiments, the subjects to be treated may have genetically influenced cutaneous milieus, which makes them susceptible to the effects of excess androgen and increased stress. Without intending to be limited by theory, these genetic factors alone or in combination with lifestyle and environmental stresses may trigger immune and inflammatory chemical cascades as well as interactions between the immune system and the pilosebaceous microflora to develop skin manifestations and diseases, such as acne vulgaris, hirsutism, alopecia, seborrheic dermatitis, premature photoaging, etc.

As will be recognized by those of skill in the art, the effects on the pilosebaceous unit including the sebaceous glands are generally dose dependent. In accordance with aspects of the disclosure, the topical administration of spironolactone, even when administered at higher concentrations in the topical compositions, (e.g., about 5% to about 25% by weight of the total composition, about 5.1% to about 25% spironolactone by weight of the total composition, about 7.5% to about 25% spironolactone by weight of the total composition, about 10% to about 25% spironolactone by weight of the total composition, etc.), result in reduced adverse events, as compared to systemic administration.

Pharmaceutical Compositions

The pharmaceutical compositions of the present disclosure generally comprise an effective amount of spironolactone and at least one pharmaceutically acceptable excipient. In certain embodiments, the spironolactone may be in any known form, including tautomers, geometrical isomers, optically active forms, enantiomeric mixtures thereof, pharmaceutically acceptable salts and pharmaceutically active derivatives and metabolites thereof.

Metabolites of spironolactone including 7-α-thiospironolactone (7-α-TS), 7-α-thiomethylspironolactone (7-α-TMS), and canrenone (7-α-desthioacetyl-δ-6-spironolactone), may be responsible for its anti-androgen and anti-stress activities in vivo. In certain aspects, the pharmaceutical compositions may include one or more of the spironolactone metabolites in addition to spironolactone or in place of spironolactone.

The pharmaceutical composition may be formulated in any form suitable for the intended method of administration. By way of example, for topical administration, the composition may be combined with at least one pharmaceutically acceptable excipient or carrier vehicle in any convenient and practical manner, i.e., by solution, suspension, emulsification, admixture, absorption and the like. Such procedures are routine for those skilled in the art.

In certain embodiments, the pharmaceutically acceptable excipient or carrier vehicle may be any suitable excipient or vehicle for topical use that does not interfere with the activity of the spironolactone in an undesired manner Such excipients and vehicles may include penetration enhancers, thickeners, solvents, stabilizers, emulsifying agents, buffers, preservatives, etc. Additionally, the composition may include salts, emollients, antimicrobials, fragrances, etc.

A "penetration enhancer" is an agent known to accelerate the delivery of the drug through the skin. These agents also have been referred to as accelerants, adjuvants, and absorption promoters, and are collectively referred to herein as "enhancers." This class of agents includes those with diverse mechanisms of action including those which have the function of improving the solubility and diffusibility of the drug, and those which improve percutaneous absorption by changing the ability of the stratum corneum to retain moisture, softening the skin, improving the skin's permeability, acting as penetration assistants or hair-follicle openers or changing the state of the skin such as the boundary layer.

Any suitable penetration enhancer may be used in the context of the present disclosure. By way of non-limiting example, penetration enhancers include functional derivatives of a fatty acid, which includes isosteric modifications of fatty acids or non-acidic derivatives of the carboxylic functional group of a fatty acid or isosteric modifications thereof. In one embodiment, the functional derivative of a fatty acid is an unsaturated alkanoic acid in which the COOH group is substituted with a functional derivative thereof, such as alcohols, polyols, amides and substituted derivatives thereof. The term "fatty acid" means a fatty acid that has four (4) to twenty-four (24) carbon atoms. Non-limiting examples of penetration enhancers include $C_5$-$C_{22}$ fatty acids such as isostearic acid, octanoic acid, and oleic acid; $C_5$-$C_{22}$ fatty alcohols such as oleyl alcohol and lauryl alcohol; lower alkyl esters of $C_5$-$C_{22}$ fatty acids such as ethyl oleate, isopropyl myristate, butyl stearate, and methyllaurate; di(lower)alkyl esters of $C_6$-$C_8$ diacids such as diisopropyl adipate; monoglycerides of $C_5$-$C_{22}$ fatty acids such as glyceryl monolaurate; tetrahydrofurfuryl alcohol polyethylene glycol ether; polyethylene glycol, propylene glycol; 2-(2-ethoxyethoxy) ethanol; diethylene glycol monomethyl ether; alkylaryl ethers of polyethylene oxide; polyethylene oxide monomethyl ethers; polyethylene oxide, dimethyl ethers; dimethyl sulfoxide; glycerol; ethyl acetate; acetoacetic ester; N-alkylpyrrolidone; and terpenes. Other exemplary penetration enhancers include, but are not limited to, N,N-dimethyl lauramide, fatty acids including oleic acid and neodecanoic acid, N-methyl pyrrolidone, etc.

The thickeners used herein may include anionic polymers such as polyacrylic acid (CARBOPOL® by B.F. Goodrich Specialty Polymers and Chemicals Division of Cleveland, Ohio), carboxymethylcellulose and the like.

Any suitable preservative conveniently added topical formulations may be used, and in such quantities as is taught by the art. For instance, methyl, ethyl, propyl and/or butyl p-hydroxybenzoate may be used in small amounts, normally not higher than 0.2-0.5 weight percent based on the total weight of the composition.

Stabilizing agents can be also added to the compositions. Examples of stabilizers for use in the composition include buffers, pH regulators, antioxidants, amino acids such as glycine and lysine, carbohydrates such as dextrose, mannose, galactose, fructose, lactose, sucrose, maltose, sorbitol, mannitol, etc.

Additional excipients may generally be found in United States Pharmacopeia/National Formulary (2000); Remington's The Science and Practice of Pharmacy, Meade Publishing Co. By way of example, the excipient or carrier vehicle may include a solvent, such as but not limited to purified water, glycols (e.g., hexylene glycol, propylene glycol, etc.), alcohols (e.g., ethanol, oleyl alcohol, etc.), propylene carbonate, mineral oil, and other organic, non-polar solvents.

In certain embodiments, the composition may comprise spironolactone in a foam, lotion, cream or gel carrier vehicle, which may comprise a combination of excipients described herein. By way of example, the carrier vehicle may contain Versabase™. In certain embodiments, the vehicle may comprise water, ethylhexyl stearate, emulsifying wax, tocopheryl acetate, aloe barbadensis leaf juice, disodium ethylenediaminetetraacetic acid, sorbitol, cyclopentasiloxane, methylchloroisothiazolinone, and methylisothiazolinone.

The actual dosage amount of a composition of the present disclosure may be determined by physical and physiological factors such as body weight, severity of condition, the type of disease being treated, previous or concurrent therapeutic interventions, idiopathy of the subject, and on the route of administration (i.e., topical administration). Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 5% of spironolactone. In other embodiments, the composition may comprise between about 5% to about 25.0% spironolactone by weight of the composition, about 5.1% to about 25% spironolactone by weight of the total composition, about 7.5% to about 25% spironolactone by weight of the total composition, about 10% to about 25% spironolactone by weight of the total composition, etc. In certain embodiments, the composition may comprise about 5%, about 5.1%, about 5.5%, about 7.5%, about 10%, about 15%, about 20%, and any range derivable therein, spironolactone by weight of the total composition. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Combination Therapy

It is also possible to combine spironolactone with any other topical agent for use in the treatment or alleviation of a disease, disorder, or condition related to excess androgen or stress-induced cutaneous changes, including compounds, in a unitary dosage form, or in separate dosage forms intended for simultaneous or sequential administration to a subject in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the treatment or alleviation of a disease, disorder, or condition related to excess androgen and other hormones.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate topical formulations. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Topical spironolactone is formulated in a Versabase™ cream carrier, and applied twice daily directly to affected areas of the cutis. Following repeated treatment of a subject in need, the following observations are expected.

Skin Conditions:

Following one month of treatment with cream applied twice daily to affected skin areas, a reduction in inflammatory papules, pustules, comedones, cysts, and seborrhea is expected to be observed.

Hair Growth:

Following six months of treatment with the cream applied in the beard distribution area, a reduction in the number of terminal hairs present is expected to be observed.

Alopecia:

Following six months of treatment with the foam or solution applied to the scalp, an increase in the caliber of the hairs is expected to be observed, thus aiding in treatment of alopecia.

Seborrheic Dermatitis:

Following two months of treatment with cream applied twice daily to affected areas, a reduction of erythema, pruritus, and rash, in the form of yellow-white greasy flakes, is expected to be observed, thus aiding in the treatment of seborrheic dermatitis.

Overall Outcomes:

Importantly, with all treatments, reduced adverse effects, as compared to systemic administration is expected. Moreover, a measurable, statistically significant improvement in psychological morbidity and quality of life for subjects is expected. The relationship between the skin and mental health is an intimate one; skin disease is a unique malady of the human condition, in that the sufferer must wear the disease daily in public. Adolescents suffer equally if not more from dermatologic conditions at a tender time of development; therefore, not addressing these whole-person concerns can have far-reaching psychological morbidity.

All publications, patents and patent applications are herein incorporated by reference to the same extent as if each individual publication, patent or patent application was specifically and individually indicated to be incorporated by reference.

What is claimed is:

1. A method for treating or alleviating symptoms of sex hormone replacement in a subject undergoing gender reassignment, wherein the symptoms are selected from inflammatory papules, pustules, comedones, cysts, seborrhea, alopecia, and any combination thereof, the method comprising topically administering a pharmaceutical composition comprising about 20% to about 25% spironolactone by weight of the total composition.

2. The method of claim 1, wherein the pharmaceutical composition comprises about 22% spironolactone by weight of the total composition.

3. The method of claim 1, wherein the spironolactone is present in an amount effective to affect the microflora of the pilosebaceous unit.

4. The method of claim 1, wherein the symptom is alopecia.

* * * * *